(12) United States Patent
Kersting et al.

(10) Patent No.: US 9,189,849 B2
(45) Date of Patent: Nov. 17, 2015

(54) METHOD AND APPARATUS FOR MULTI-LEVEL EYE REGISTRATION

(75) Inventors: Oliver Kersting, Kleinmachnow (DE);
Horia Grecu, Bukarest (RO)

(73) Assignee: Alcon Pharmaceuticals Ltd., Fribourg (CH)

( * ) Notice: Subject to any disclaimer, the term of this patent is extended or adjusted under 35 U.S.C. 154(b) by 268 days.

(21) Appl. No.: 13/989,501

(22) PCT Filed: Nov. 25, 2011

(86) PCT No.: PCT/EP2011/071009
§ 371 (c)(1),
(2), (4) Date: Aug. 29, 2013

(87) PCT Pub. No.: WO2012/069624
PCT Pub. Date: May 31, 2012

(65) Prior Publication Data
US 2013/0336559 A1    Dec. 19, 2013

(30) Foreign Application Priority Data
Nov. 26, 2010   (EP) ..................................... 10192818

(51) Int. Cl.
| G06T 7/00 | (2006.01) |
| A61B 3/113 | (2006.01) |
| A61B 3/15 | (2006.01) |
| A61F 9/007 | (2006.01) |

(52) U.S. Cl.
CPC .............. G06T 7/0016 (2013.01); A61B 3/113 (2013.01); A61B 3/152 (2013.01); G06T 7/0028 (2013.01); A61F 9/007 (2013.01); G06T 2207/30041 (2013.01)

(58) Field of Classification Search
None
See application file for complete search history.

(56) References Cited

U.S. PATENT DOCUMENTS

| 4,922,909 | A  | * | 5/1990  | Little et al. ..................... 600/300 |
| 5,912,720 | A  |   | 6/1999  | Berger et al. |
| 6,276,798 | B1 | * | 8/2001  | Gil et al. ........................ 351/206 |
| 2003/0135115 | A1 | * | 7/2003  | Burdette et al. .............. 600/437 |
| 2004/0143244 | A1 | * | 7/2004  | Gray et al. ........................ 606/5 |
| 2004/0254441 | A1 |   | 12/2004 | Schrunder |

(Continued)

FOREIGN PATENT DOCUMENTS

| CN | 1650148 | 8/2005 |
| CN | 1774207 | 5/2006 |

(Continued)

*Primary Examiner* — Vu Le
*Assistant Examiner* — Alexander J Lesnick
(74) *Attorney, Agent, or Firm* — Haynes and Boone, LLP

(57) ABSTRACT

A method for performing multi-level eye registration comprising: obtaining a first initial reference eye image by a first diagnostic device and defining a reference coordinate system; obtaining a second eye image by a surgery device, said second eye image being obtained in a pre-surgery phase before the surgery has started; performing a first registration between said first eye image and said second eye image to obtain a first registration result; obtaining a third eye image by said surgery device, said third eye image being obtained after surgery has started; performing a second registration between said second eye image and said third eye image to obtain a second registration result; combining said first and second registration results to obtain a combined registration result to thereby obtain a registration between said initial reference eye image obtained by said diagnostic device and said third eye image obtained by said surgery device after surgery has started.

20 Claims, 3 Drawing Sheets

(56) References Cited

U.S. PATENT DOCUMENTS

| | | | |
|---|---|---|---|
| 2009/0080737 A1* | 3/2009 | Battle et al. | 382/131 |
| 2009/0088773 A1* | 4/2009 | Zhao et al. | 606/130 |
| 2009/0316112 A1* | 12/2009 | Neal et al. | 351/246 |
| 2010/0082017 A1* | 4/2010 | Zickler et al. | 606/4 |
| 2010/0110379 A1* | 5/2010 | Zhou et al. | 351/211 |

FOREIGN PATENT DOCUMENTS

| | | | |
|---|---|---|---|
| EP | 2 184 005 | 5/2010 | |
| EP | 2184005 A1 * | 5/2010 | ............. A61B 3/113 |
| WO | WO 01/89373 | 11/2001 | |
| WO | WO 02/082981 | 10/2002 | |

* cited by examiner

METHOD AND APPARATUS FOR MULTI-LEVEL EYE REGISTRATION

CROSS-REFERENCE TO RELATED APPLICATION

This application is a United States national phase application of co-pending international patent application number PCT/EP2011/071009, filed Nov. 25, 2011, which claims the benefit of EP Application No. 10192818.2 filed Nov. 26, 2010, the disclosure of which is incorporated herein by reference.

FIELD OF THE INVENTION

The present invention relates to a method and an apparatus for multi-level eye registration.

BACKGROUND OF THE INVENTION

Tracking and registration of an eye position is known to be used for several applications in ophthalmic surgery and diagnostics. However, the majority of solutions offer only partial results, in the sense that they are only applicable within the same device or within a particular combination of devices. The current ophthalmic care procedures are complex processes that involve a plurality of tools in varying contexts that create significant impact on the eye appearance. Some of these impacts even prohibit the application of current registration techniques. Being able to relate the various measurements in a unified way presents a significant challenge.

Currently, there are multiple new surgery techniques that imply a fully fixated eye relative to the treatment device, e.g. femtosecond laser for corneal procedures, microwave deforming devices for corneal treatments, or femtosecond laser for cataract surgery. All these surgery techniques have in common the fact that the treatment zone is placed relative to a suction ring on the eye. In the coordinate system of the suction ring, the eye can be treated with automatic means that achieve treatment positioning precision that is far better than any manual one.

This means that using a suction ring coordinate system the eye can be treated with a spatial precision that is far better than the mechanical precision of a surgeon. But: In the overall diagnostic-treatment process, the placement of the suction ring on the eye may induce significantly higher errors than the reduction of the error which automated treatment may achieve, because:
  a) The Placement of the ring is not accurately controllable:
    The procedure is done manually by the surgeon, thus being limited by general human mechanical abilities. During the suction process, the suction ring slides slightly on the cornea until it is fixed relative to the eye, thus always introducing errors with respect to the desired position.
  b) Actual placement of the ring is difficult to measure:
    The eye is deformed by the unnatural pressure, which impacts the capabilities of measuring the eye biometry (e.g. corneal shape) after the suction ring is placed. Natural landmarks on the eye (e.g. sclera features, limbal border) are covered by the tool mechanics (e.g. suction ring). Therefore a manual visual alignment of the ring by the doctor is hard to achieve.
  c) Manual measurement and adjustment of treatment zone takes time:
    The suction ring placement time and the time for manual adjustment of the treatment zone can be longer than the treatment time itself. Stress and dehydration of the patient's eye may interfere with the physical and mechanical assumptions for the (laser) treatment.

Consequently, the high precision of the new generation treatment devices is an instable promise, due to the errors and uncertainties induced as mentioned before in connection with the placement of the suction ring.

The proof of clinical outcome improvement with these new generation devices depends on a reliable basis for documenting and analyzing surgery with post-surgery results. It is therefore an object of the invention to provide a method and an apparatus, which can reduce these negative effects of the errors induced by the suction ring.

SUMMARY OF THE INVENTION

According to one embodiment there is provided a method for performing eye registration comprising:
  obtaining a first initial reference eye image by a first diagnostic device and defining a reference coordinate system;
  obtaining a second eye image by a surgery device, said second eye image being obtained in a pre-surgery phase before the surgery has started;
  performing a first registration between said first eye image and said second eye image to obtain a first registration result;
  obtaining a third eye image by said surgery device, said third eye image being obtained after surgery has started;
  performing a second registration between said second eye image and said third eye image to obtain a second registration result;
  combining said first and second registration results to obtain a combined registration result to thereby obtain a registration between said initial reference eye image obtained by said diagnostic device and said third eye image obtained by said surgery device after surgery has started.

According to one embodiment said first eye image taken by said diagnostic device and said third eye image taken by said surgery device are taken under significantly different eye conditions which can negatively affect a direct registration between said first eye image and said second image. According to one embodiment there is provided a method for performing eye registration comprising:
  obtaining a first initial reference eye image by a first diagnostic device and defining a reference coordinate system;
  obtaining a second eye image by a surgery device, said second eye image being obtained in a pre-surgery phase before the surgery has started;
  performing a first registration between said first eye image and said second eye image to obtain a first registration result;
  obtaining a third eye image by said surgery device, said third eye image being obtained after surgery has been completed;
  performing a second registration between said second eye image and said third eye image to obtain a second registration result;
  combining said first and second registration results to obtain a combined registration result to thereby obtain a registration between said initial reference eye image obtained by said diagnostic device and said third eye image obtained by said surgery device after surgery has been completed.

By providing multiple registration steps, which are then combined one, can overcome the large difference between the first and third image, which makes a direct registration between these two images difficult.

According to one embodiment said first eye image taken by said diagnostic device and said third eye image taken by said surgery device are taken under significantly different eye conditions which can negatively affect a direct registration between said first eye image and said third image. The different eye conditions can be overcome by the combined multi-level registration process. For that purpose there is performed an intermediate registration step using the second image which is taken under eye conditions which are less significantly different from the eye conditions under which the first image was taken than the eye conditions under which the third image was taken. In this manner the registration becomes possible and more accurate by introducing an intermediate registration step which can be more easily executed than a direct registration between the first and the third image, since the differences in eye conditions between first and second and between second and third image, respectively, are less significant than the differences in eye conditions between the first and the third image.

According to one embodiment said different eye conditions comprise:

the eye having no tool or object which fully or partially occludes the eye when said first image is taken and the eye having a tool which fully or partially occludes the eye when the third image is taken; or the eye having no suction ring being placed on it when said first image is taken, the eye having no suction ring being placed on it when said second image is taken and the eye having a suction ring being placed on it when the third image is taken.

This is an example of significantly different eye conditions, which would make a direct registration difficult.

According to one embodiment said different eye conditions comprise:

the eye showing no influences of the surgical treatment procedure on the patient's eye when said first image is taken, and the eye showing no influences of the surgical treatment procedure on the patient's eye when said second image is taken, and the eye showing influences of the surgical treatment procedure on the patient's eye when said third image is taken.

This is another example of significantly different eye conditions, which would make a direct registration difficult.

According to one embodiment said influences the treatment procedure on the patient's eye comprise one or more of the following:

bleedings, deformations of the eyeball from the suction ring, ablation bubbles under or in the cornea covering the iris, color changes of the cornea or iris due to treatment impacts;

a tool or object which fully or partially occludes the eye.

These are other examples of significantly changed eye conditions, which would make a direct registration between the first and the third image difficult.

According to one embodiment the method further comprises:

performing a registration from a post-surgery images taken by said surgery device to a post-surgery diagnostic image taken by a diagnostic device; and/or performing a registration from said diagnostic reference image to one or more post-surgery diagnostic images.

This further enhances the registration scope over multiple phases of ophthalmic treatment/diagnosis.

According to one embodiment the registration steps are performed by identifying one or more eye features in the two eye images, which are to be registered to thereby determine the coordinate relationship between the two pictures, wherein the eye features which are used for the different registration steps are selected appropriately in accordance with the different modalities in the different registration steps.

The selection of suitable features depending on the context of the individual registration step adapts the method to the specific conditions of a given scenario and enhances its performance.

According to one embodiment the first registration step is performed between two images being taken by two different devices, possibly under different instrumentational operating modalities (such as different illumination wavelength, different camera, different microscope, etc.), but with the eye being in the same or substantially the same condition. In other words, the eye condition is not yet affected by the surgery or preparatory steps for the surgery, such as the placement of a suction ring, which could significantly change the eye condition in a way which would increase the difficulty of registration. On the other hand, the second registration step is performed between two images taken by the same device under the same or substantially the same instrumentational operation modalities (such as the same illumination wavelength, the same camera, the same microscope, etc.), but at eye conditions which are significantly different due to the effect of the surgery or the preparatory actions of the surgery so that the different eye conditions increase the difficulty of registration. In this manner the individual difficulty of the first and the second registration steps are less than the direct registration from the first to the third image. Therefore, the accuracy of the first and the second registration steps can be enhanced, and therefore by combining the first and the second registration step to a combined registration step the overall accuracy of the registration can be increased compared with a direct registration between the first and the third image.

According to one embodiment, from the first to the third image there are two changes which both increase the difficulty of a direct registration between the first and the third image, namely a first change from the first image to the second image caused by the change from the diagnostic device taking the first image to the surgical device taking the second image, and a second change from the second image to the third image caused by the change of the eye condition due to the start of the surgery, and wherein to avoid a direct registration from the first to the third image which could suffer from accuracy due to the accumulated effects of said first and second changes, a first registration between said first and said second image and a second registration between said second and said third image are preformed and combined to a combined registration to obtain a registration between said first and said third image.

According to one embodiment the features which are used for registering the initial diagnostic image taken by said diagnostic device and the pre-surgery image taken by said surgery device are limbus and sclera features;

the features which are used for registering the pre-surgery image taken by said surgery device and the intra-surgery image taken by said surgery device are iris and/or pupil features;

the features which are used for registering the pre-surgery image taken by said surgery device and the post-surgery image taken by said surgery device are one or more of iris, pupil, limbus, or sclera features.

These are examples of suitable features, which may be selected depending on a given scenario.

According to one embodiment an apparatus for performing an eye registration comprises: a module for obtaining a first initial reference eye image by a first diagnostic device and defining a reference coordinate system;

a module for obtaining a second eye image by a surgery device, said second eye image being obtained in a pre-surgery phase before the surgery has started;

a module for performing a first registration between said first eye image and said second eye image to obtain a first registration result;

a module for obtaining a third eye image by said surgery device, said third eye image being obtained after surgery has started;

a module for performing a second registration between said second eye image and said third eye image to obtain a second registration result;

a module for combining said first and second registration results to obtain a combined registration result to thereby obtain a registration between said initial reference eye image obtained by said diagnostic device and said third eye image obtained by said surgery device after surgery has started.

According to one embodiment an apparatus for performing eye registration comprises:

a module for obtaining a first initial reference eye image by a first diagnostic device and defining a reference coordinate system;

a module for obtaining a second eye image by a surgery device, said second eye image being obtained in a pre-surgery phase before the surgery has started;

a module for performing a first registration between said first eye image and said second eye image to obtain a first registration result;

a module for obtaining a third eye image by said surgery device, said third eye image being obtained after surgery has been completed;

a module for performing a second registration between said second eye image and said third eye image to obtain a second registration result;

a module for combining said first and second registration results to obtain a combined registration result to thereby obtain a registration between said initial reference eye image obtained by said diagnostic device and said third eye image obtained by said surgery device after surgery has been completed.

According to one embodiment the apparatus comprises:

a module for carrying out a method according to one of the embodiments of the invention.

According to one embodiment there is provided a computer program which when being executed on a computer enables said computer to carry out a method according to one of the embodiments of the invention.

DETAILED DESCRIPTION

Figure 1:
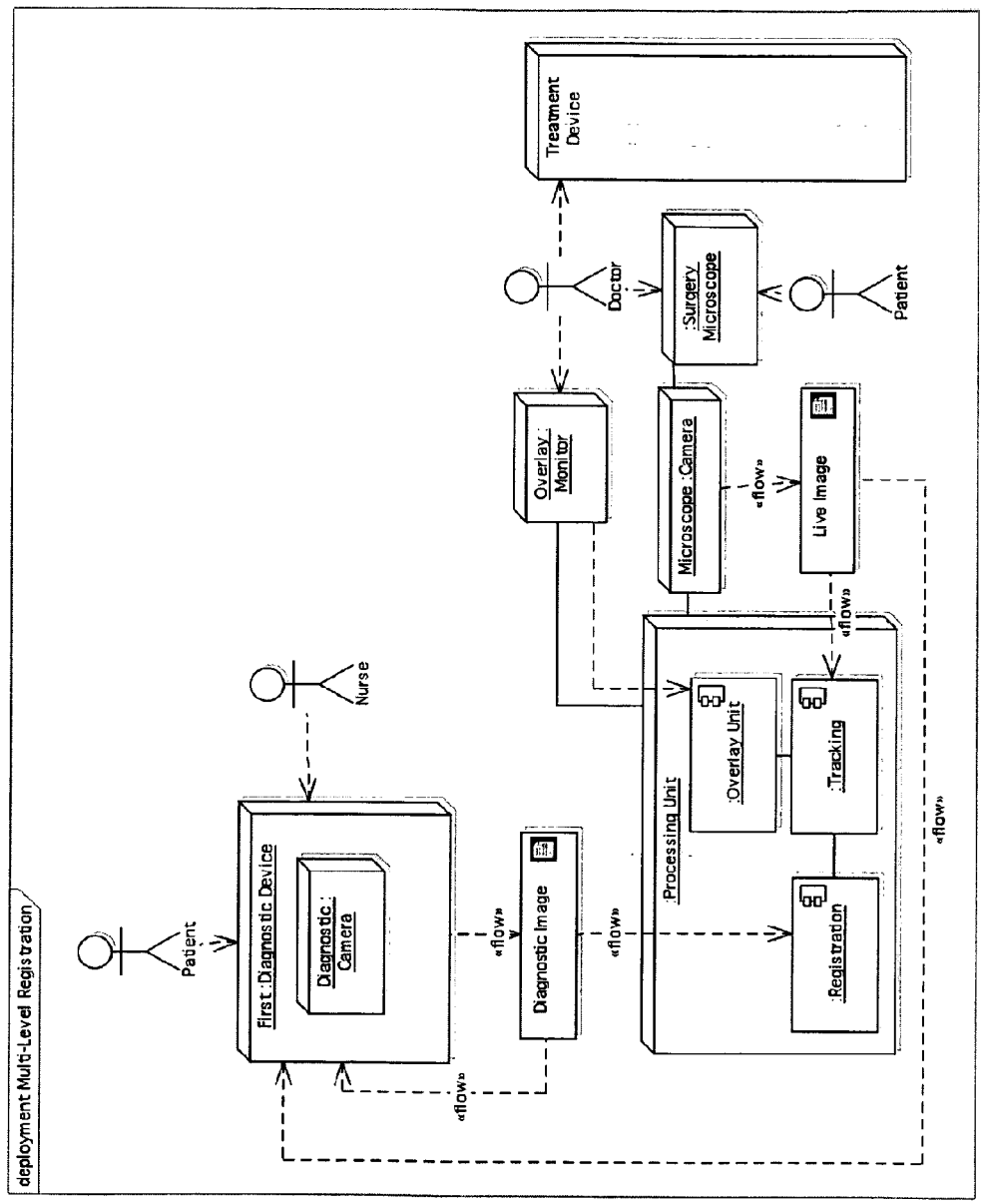
FIG. 1 schematically illustrates a system implementing a registration process according to an embodiment of the invention.

The errors and uncertainties which are caused by a suction ring placed on an eye can be reduced if there is provided an approach, which can fill the missing link from the diagnostic coordinate system to the intra-surgery coordinate system. Embodiments of the invention provide an approach to fill this gap in a manner, which will be described in more detail later.

According to embodiments of the invention there can be used for determining a consistent eye coordinate system as well as the position of various features within the eye coordinate system during multiple phases of ophthalmic diagnostic/treatment processes (collectively termed as ophthalmic care). This relates to the diagnostic phase, the pre-surgery phase, the intra-surgery phase and the post surgery phase.

The eye coordinate system as well as specific eye features (limbal ring, pupil, iris, sclera vessels, markers) can be determined from different imaging modalities, at different points in time and over varying eye conditions in interaction with varying tools (e.g. suction ring) and procedures which may significantly affect the imaging content. The eye registration process according to an embodiment is split up into a plurality of individual registration steps, each leading to a registration result, and then the multiple registration results are combined into a combined registration result, which yields higher accuracy and overcomes the difficulties of the prior art.

Embodiments of the invention therefore may provide a method capable of registering the eye throughout various phases of treatment and diagnostics by combining multiple levels of registration to ensure:

1. Accurate toric (rotational) alignment of treatment areas and spots
2. Accurate centration of treatment areas and spots
3. Verification of intended and actual treatment areas and spots
4. Spatially consistent measurements of post-surgery diagnostics relative to pre-surgery diagnostics (e.g. determination of implants, cuts, treatments relative to diagnostic)
5. Correlation of post-surgery spatial variations of intended treatment with patient visual outcome In order to achieve these advantageous effects according to one embodiment of the invention there is made use the following features:

Performing a multi-step registration combining multiple registration results of eye images determined in different points in time.

According to one embodiment the approach further comprises:

Using a linked chain of imaging devices that can exchange data via suitable interfaces (e.g. corneal diagnostic device linked with processing unit analyzing microscope camera images).

Performing a multi-feature registration using a context sensitive feature extraction and registration depending on the modality of the image and of the eye conditions (e.g. eye coverage, deformations, bleedings)

These approaches may be summarized and referred to in the following more detailed description of embodiments as "Multi-Level Registration", because the registration is performed for different combinations of phases of the ophthalmic care procedure, and these different registration steps (or levels) are then combined to achieve a more comprehensive registration with higher accuracy.

To explain the significance of this approach in somewhat more detail reference is once again made to the prior art registration approach. In the prior art eye registration complexity is driven mainly by the difference in imaging modalities between diagnostic and/or surgery imaging devices (e.g. different light wavelength, field-of-view, camera resolution, camera location, integration time). The difference in the eye conditions (e.g. deformation, bleedings, and occlusions by tools) is typically neglected in current registration implementations, because the doctor is forced to ensure similar eye conditions by the process.

But—as was explained above—there are processes that require a consistent and accurately determined coordinate system throughout all steps, but do not ensure similar eye conditions over these steps. The registration system according to embodiments of the present invention can deal with different image modalities and similar eye conditions as well as with similar image modalities and different eye conditions. Together with repeatedly applied registration steps, this becomes an effective "full process coordinate system"-device.

A linked chain of imaging devices that can exchange data via interfaces are the platform for applying this invention according to one embodiment which will now be described in connection with FIG. 1. The first device involved in the process is a Diagnostic Device that—besides measurements—provides an initial reference image of the patient eye that serves as the origin of the coordinate system for the overall process that follows.

The Processing Unit shown in FIG. 1 (which may be any standard computer suitably programmed) receives the initial reference image and is linked to the imaging system of the surgery microscope in the operating room. The reference image information is imported by a Processing Unit and stored for upcoming registration steps. The diagnostic (initial) reference image is used for registering the live surgery image directly to the reference coordinate system or, according to an embodiment of the invention, indirectly, via an already registered reference image from the surgery image stream. The direct registration is illustrated in FIG. 1 by the live stream being fed to the processing unit and therein it is processed by a tracking module, which compares it with the initial reference image for registration/tracking.

According to one embodiment, however, the registration is not carried out directly but via an intermediate step using an already registered image from the surgery image stream. For that purpose there is at first taken an image of the surgery image stream, which is captured before the surgery actually started, i.e. in the pre-surgery phase. The term "pre-surgery" here refers to the fact that the effects of the surgery, which could negatively affect registration, e.g. the deformation or partial coverage of the eye due to the placement of a suction ring, the bleeding due to incisions, etc., have not yet taken place. The eye image is taken by the surgical device, but in the state, which precedes the surgery, itself and also the preparatory actions for the surgery such as the placement of a suction ring.

In such a pre-surgery state the eye image is more "close" in its character to the initial reference image taken by the diagnostic device in order to determine the initial reference coordinate system. Therefore it is easier and more accurate to perform a registration between the initial reference image and the pre-surgery image than between the initial reference image and the intra-surgery image.

The registration between the initial reference image and the pre-surgery image then leads to a first registration result which consists of a coordinate relationship (or lateral and rotational "displacement") between the initial reference coordinate system in the initial reference image and the coordinate system (or the location of the eye) in the pre-surgery image.

In a next step then there is carried out a second registration between the pre-surgery image and an "intra-surgery image" which is taken by the surgical device during the surgery, and especially in a condition which affects the eye image, e.g. due to the placement of a suction ring, the deformation of the eye, the bleeding of the eye due to incisions, etc. However, since the "modalities" which means the device arrangement (camera, microscope, wavelength of illumination, etc.) are identical for the pre-surgery and the intra-surgery image, it is easier to perform a registration between pre-surgery image and intra-surgery image than between the intra-surgery image and the initial (diagnostic) reference image which may have been taken by a completely different device under different conditions such as another illumination wavelength, another camera, etc.

The second registration then yields a second registration result, which consists of a coordinate relationship (or lateral and rotational "displacement") between the reference coordinate system in the pre-surgery image and the coordinate system (or the location of the eye) in the intra-surgery image.

The first and the second registration result can then be combined to obtain a combined registration result (which can be easily obtained just by vector addition of the displacement vectors of the two registration steps), and the combined registration result then effectively yields a registration between an initial diagnostic reference image and an intra-surgery image. This approach can then be used to perform the "two-step" or "multi-level" registration also for the further intra-surgery live images, and in this way a more effective tracking based on the initial diagnostic image and the intra-surgery live stream can be achieved.

According to one embodiment the registered surgery live images can be exported for future post-op follow-up analysis of clinical process outcome.

As describe in the previous embodiment, multi-step or multi-level registration combines multiple registration results of eye images determined in different points in time for providing transformation changes over complete diagnostic and surgery processes.

Figure 2:
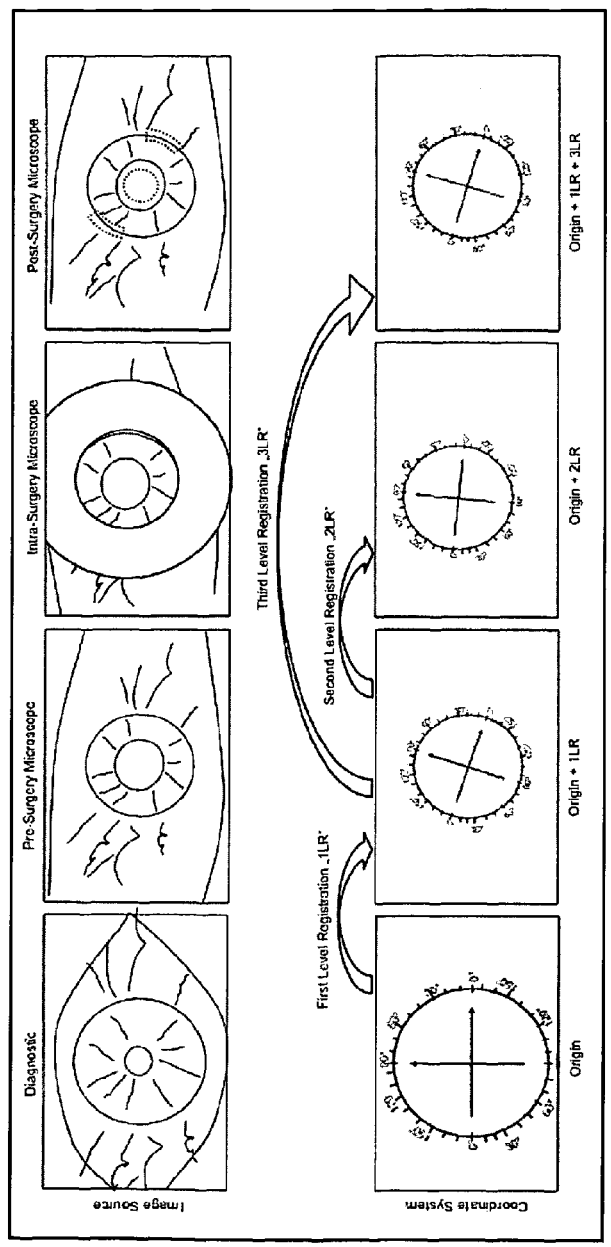
FIG. 2 schematically illustrates a multi-level registration process according to an embodiment of the invention.

FIG. 2 illustrates further embodiments with 3 different types of registrations, which allow a coordinate system reference at every point in time in the surgery.

The 1 LR (first level registration) shows the registration from the diagnostic image taken by the diagnostic device to the pre-surgery microscope image. There are some modality changes from diagnostic device to the surgery microscope which have to be addressed (e.g., differences in wavelength can be addressed by concentrating on wavelength independent signals, differences in optics can be addressed by calibration of both devices). However, typically the eye conditions are similar, except the insertion of a speculum to keep the eye lids open and the dilation or shrinking of the pupil using drugs on the surgery side. The 1 LR provides the extra-device registration result, i.e. the registration from the diagnostic device to the surgery device.

The 2LR (second level registration) shows the registration on the same device—the surgery microscope—from the pre-surgery microscope image to the intra-surgery microscope image. A direct registration from the intra-surgery microscope image to the diagnostic reference image would likely fail or be inaccurate, due to the significant coverage and deformation of eye features by the suction ring: Modality (e.g. change of wavelength, camera, etc.) and eye conditions (placement of suction ring) in combination are just too different. However, registering of the intra-surgery image to the pre-surgery microscope image is feasible due to the similarity of the image modalities (e.g. same light wavelength) and the eye features (e.g. same pupil size, same iris shape). With the combination of 2LR and 1 LR there can be obtained a combined registration result and thereby the link from the intra-surgery coordinate system to the diagnostic reference image coordinate system can be established.

The 3LR (third level registration) shows the registration on the same device—the surgery microscope—from the pre-surgery microscope image to the post-surgery microscope image. A direct registration from the intra-surgery microscope image to the diagnostic reference image is difficult and inaccurate, due to the influences the treatment procedure has on the patient's eye (e.g. bleedings, deformations of the eye ball from the suction ring, ablation bubbles under or in the cornea covering iris). Registering to the pre-surgery microscope image, however, is feasible due to the similarity of the image modalities (e.g. same light wavelength) and eye features (e.g. same pupil size, same iris shape). With the combination of the two registration results 3LR and 1 LR the link to the diagnostic reference image coordinate system can be established.

Beyond the registration levels shown in FIG. 2 the registration from the post-surgery microscope images to a post-surgery diagnostic image and/or from the pre-surgery diagnostic reference image to one or more post-surgery diagnostic image are be feasible just by adding a further registration step to the combined registration.

The particular chain of registration steps required to be performed by the system in order to achieve the desired coordinate system mapping, can be either a-priori defined, or automatically selected by the system based on the knowledge of performance of each registration step. E.g., on a specific image pair taken out of a known step of the surgery process, the system can iterate over sequence of registration algorithm types (e.g. iris-iris registration, sclera-sclera registration) to determine the highest quality confidence of the registration result on the specific image pair. The sequence of registration algorithm types can be pre-defined in the system depending on the knowledge of the individual surgery step.

Figure 3:
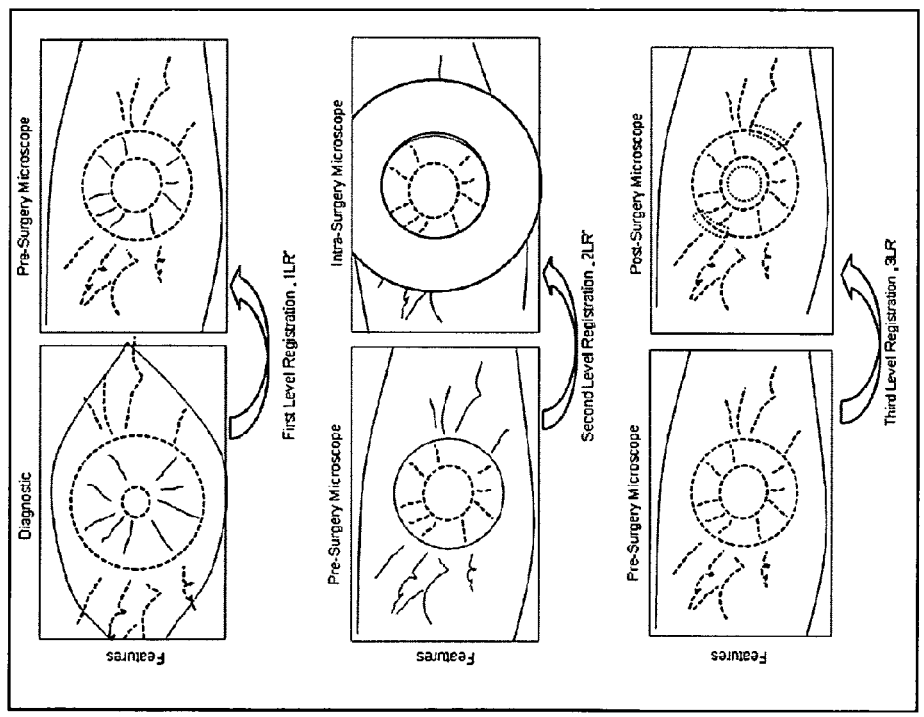
FIG. 3 schematically illustrates the eye features used in a multi-level registration process according to an embodiment of the invention.

According to one embodiment multi-feature registration extracts context sensitively different type of eye features from diagnostic or surgery images, to achieve robust and reliable registration results over varying imaging modalities and eye conditions. This means that, depending on the actual registration step (e.g. 1 LR, 2LR, 3LR) and the modalities, which are applied in the respective step, the most suitable features are selected and used for the registration procedure. FIG. 3 illustrates this by showing different examples of multi-feature registration on eye images. The registration steps shown in FIG. 3 are 1 LR (top), 2LR (middle), and 3LR (bottom). The features which are taken into account for the registration are dashed in FIG. 3.

The images pairs in FIG. 3 for 1 LR (top) show the feature extraction according to one embodiment from a diagnostic device to a microscope image. In the given example the diagnostic image was taken with white or green light while the microscope image was taken with white light. Typically the patient eye in the diagnostic image is not manipulated with drugs to show a small or large pupil, neither are the eye lids clamped. During surgery typically the eye is opened by a speculum and the pupil is dilated to its maximum. For registering the coordinate system in this case from the diagnostic to the surgery modality and conditions, the preferable reliable features are limbus and sclera features (blood vessels). Doing that, the projection of the diagnostic pupil into the surgery image is feasible (pupil center shift compensation) as well, because the diagnostic pupil location relative to the limbus is know from the diagnostic image, the limbus in the surgery image is known and the cyclotorsion between the diagnostic and surgery image is known.

The images pairs in FIG. 3 for 2LR show the feature extraction from a pre-surgery microscope image to an intra-surgery microscope eye image, here covered with a suction ring. The suction ring mechanics typically cover parts of the limbus and most of the sclera area. Fortunately the pupil diameter and position is fixed due to eye drugs between the two images. Therefore iris and pupil features from a pre-surgery microscope image and the intra-surgery microscope image can be used to fully register the lateral and torsional position of the two images.

Combining 1 LR and 2LR the link between the diagnostic reference image and the intra-surgery microscope image can be reliably established. Referring to the suction ring example, this method brings all alignment information (e.g. pupil center shift, mesopic pupil, astigmatism) automatically from the diagnostic analysis to the intra-suction ring phase.

The image pairs in FIG. 3 for 3LR show the feature extraction from a pre-surgery microscope image to a post-surgery microscope image. Due to the identical image modality and the "tool cleaned" eye, the treatment impacts (e.g. bleeding, bumps, deformations) do not prohibit the registration using all eye features.

The foregoing examples show that combining separate registration steps, an preferably also applying context sensitively different eye features for registration allows dealing with the barriers implied by image modalities and eye condition difference over the diagnostic and surgery process. One may therefore say that according to one embodiment there is provided an approach which enables a registration between two situations (a first situation and a second situation) in which there is such a significant difference of the eye condition and/or the used device(s) or its modality (such as wavelength or optics) that a direct registration between the eye in these two situations cannot be performed or is at least very difficult and prone to errors. To enable such a registration between these two significantly different situations, according to one embodiment there is provided an "intermediate registration step" (e.g. the step 1 LR) for which there may be some change of the device or its modality (like a frequency change or change in optics), e.g. due to the change form one device (diagnostic device) to another (the surgery device), and/or a change of the eye condition (e.g. the introduction of a speculum), however, the intermediate situation is chosen such that this change of the modality and/or eye condition is less significant than it is for the change from the first to the second situation for which a direct registration is not possible. Then, a second registration step is performed between the intermediate situation and the second situation, for which the change of the device and/or its modality and/or the eye condition is also less significant (in terms of its significance for the performance or the accuracy of the registration) than it is for the change from the first to the second situation. By combining the intermediate registration and the second registration one may then obtain the registration between the first and the second situation.

As described in the embodiments before, the first situation may be a situation where a diagnostic device is used, the second situation may be an intra-surgery situation where a surgery device is used and the eye condition is changed significantly e.g. due to a suction ring placement, and the intermediate situation may be the "pre-surgery condition of the eye before the placement of the suction ring but in a situation where the surgical device is used, in other words a situation where the surgery itself has not yet started and the preparatory work which significantly changes the eye condition, like e.g. the placement of a suction ring, also has not been carried out. The particular set of features selected to perform each registration step in order to achieve the desired coordinate system mapping, can be either a-priori defined, or automatically selected by the system based on the context sensitive knowledge of performance of each feature.

The embodiments described before yield several advantages over the prior art, for example:

Current approaches for eye registration are dealing with modality changes of the imaging devices, but they are not deal with intra-device eye condition changes, such as the placement of a suction ring.

Using multiple registration steps, preferably in connection with context sensitive determination of adequate eye features used for registration, increases the overall accuracy and robustness from diagnostic to surgery, from surgery to diagnostic, from pre-surgery diagnostic to post-surgery diagnostic and post-surgery diagnostic to post-surgery diagnostic.

Automatic determination of optimal sequence of registration steps and context dependent eye features, insures optimal overall robustness & accuracy tradeoff. The optimal sequence can e.g. be determined by knowing the likelihood of success (robustness) and accuracy that can be expected for any pair of images. For example, based on prior clinical data, it can be determined that the likelihood of success of registering first image to second image is XY %, the likelihood of success of registering second image to third is YZ % and the likelihood of success of registering first image to third is XZ %. Then, the system can determine if XY %<*>YZ %>XZ %, i.e. if it is appropriate to consider the combination of the two registration steps or the direct registration step. In the same way, by comparing known likelihood of success of different eye features in the context (i.e. likelihood of iris registration vs. sclera registration between a diagnostic and a intra-surgery image) the algorithm can decide the most appropriate features to use on each particular step. This decision may also take into account computational considerations, i.e. how fast each of the features is registered.

Replacing the manual tool positioning (e.g. suction ring) saves serious surgery treatment time for the patient and the surgeon Post-surgery diagnostic follow-up performed always relative to the same (!) coordinate system defined at the beginning of the process will improve the post-surgery analysis of eye surgeries of treatments with lasers and/or implants.

It will be understood by the skilled person that the embodiments described hereinbefore may be implemented by hardware, by software, or by a combination of software and hardware. The modules and functions described in connection with embodiments of the invention may be as a whole or in part implemented by microprocessors or computers which are suitably programmed such as to act in accordance with the methods explained in connection with embodiments of the invention. This may involve the connection of such computers or microprocessors with suitable interfaces and/or measuring and/or treatment devices as they are used in the field of ophthalmic diagnostics and treatment, as will be readily understood by the skilled person.

The invention claimed is:

1. A method for performing eye registration comprising:
   obtaining a first initial reference eye image by a first diagnostic device and defining a reference coordinate system;
   obtaining a second eye image by a surgery device, said second eye image being obtained in a pre-surgery phase before the surgery has started;
   performing a first registration between said first eye image and said second eye image to obtain a first registration result;
   obtaining a third eye image by said surgery device, said third eye image being obtained after surgery has started;
   performing a second registration between said second eye image and said third eye image to obtain a second registration result;
   combining said first and second registration results to obtain a combined registration result to thereby obtain a registration between said initial reference eye image obtained by said diagnostic device and said third eye image obtained by said surgery device after surgery has started;
   wherein said first eye image taken by said diagnostic device and said third eye image taken by said surgery device are taken under significantly different eye conditions that can negatively affect a direct registration between said first eye image and said third eye image, the different eye conditions comprising the eye having no tool which fully or partially occludes the eye when said first image is taken and the eye having a tool which fully or partially occludes the eye when the third image is taken.

2. The method of claim 1, wherein said different eye conditions comprise:
   the eye having no suction ring being placed on it when said second image is taken and
   the eye having a suction ring being placed on it when the third image is taken.

3. The method of claim 1, wherein said different eye conditions comprise:
   the eye showing no influences of the surgical treatment procedure on the patient's eye when said first image is taken,
   the eye showing no influences of the surgical treatment procedure on the patient's eye when said second image is taken, and the eye showing influences of the surgical treatment procedure on the patient's eye when said third image is taken.

4. The method of claim 3, wherein said influences of the treatment procedure on the patient's eye comprise one or more of the following:
   bleedings,
   deformations of the eyeball from the suction ring,
   ablation bubbles under or in the cornea covering the iris;
   color changes of the cornea or iris due to treatment impacts;
   a tool or object which fully or partially occludes the eye.

5. The method of claim 1, further comprising:
   performing a registration from a post-surgery images taken by said surgery device to a post-surgery diagnostic image taken by a diagnostic device; and/or
   performing a registration from said diagnostic reference image to one or more post-surgery diagnostic images.

6. The method of claim 5, wherein
   the registration steps are performed by identifying one or more eye features in the two eye images, which are to be registered to thereby determine the coordinate relationship between the two pictures, wherein
   the eye features which are used for the different registration steps are selected in appropriately in accordance with the different modalities in the different registration steps.

7. The method of claim 6, wherein the features which are used for registering the initial diagnostic image taken by said diagnostic device and the pre-surgery image taken by said surgery device are limbus and sclera features;
   the features which are used for registering the pre-surgery image taken by said surgery device and the intra-surgery image taken by said surgery device are iris and/or pupil features; the features which are used for registering the pre-surgery image taken by said surgery device and the post-surgery image taken by said surgery device are one or more of iris, pupil, limbus, or sclera features.

8. The method of claim 1, wherein from the first to the third image there are two changes which both increase the difficulty of a direct registration between the first and the third image, namely a first change from the first image to the second image caused by the change from the diagnostic device taking the first image to the surgical device taking the second image, and a second change from the second image to the third image caused by the change of the eye condition due to the start of the surgery, and wherein to avoid a direct registration from the first to the third image which could suffer from accuracy due to the accumulated effects of said first and second changes, a first registration between said first and said second image and a second registration between said second and said third image are performed and combined to a combined registration to obtain a registration between said first and said third image.

9. The method of claim 1, wherein the first registration step is performed between said first and said second images being taken by two different devices but with the eye being in the same or substantially the same condition such that the eye condition is not yet affected by the surgery or preparatory steps for the surgery which would significantly change the eye condition in a way which would increase the difficulty of registration, and the second registration step is performed said second and said third images taken by the same device under the same or substantially the state instrumentational operation but at eye conditions which are significantly different due to the effect of the surgery or the preparatory actions of the surgery.

10. A method for performing eye registration comprising:
obtaining a first initial reference eye image by a first diagnostic device and defining a reference coordinate system;
obtaining a second eye image by a surgery device, said second eye image being obtained in a pre-surgery phase before the surgery has started;
performing a first registration between said first eye image and said second eye image to obtain a first registration result;
obtaining a third eye image by said surgery device, said third eye image being obtained after surgery has been completed; performing a second registration between said second eye image and said third eye image to obtain a second registration result;
combining said first and second registration results to obtain a combined registration result to thereby obtain a registration between said initial reference eye image obtained by said diagnostic device and said third eye image obtained by said surgery device after surgery has been completed;
wherein said first eye image taken by said diagnostic device and said third eye image taken by said surgery device are taken under significantly different eye conditions that can negatively affect a direct registration between said first eye image and said third image, the different eye conditions comprising the eye having no tool that fully or partially occludes the eye when said first image is taken and the eye having a tool that fully or partially occludes the eye when the third image is taken.

11. The method of claim 10, wherein said different eye conditions comprise:
the eye having no suction ring being placed on it when said second image is taken and
the eye having a suction ring being placed on it when the third image is taken.

12. The method of claim 10, wherein
said different eye conditions comprise:
the eye showing no influences of the surgical treatment procedure on the patient's eye when said first image is taken,
the eye showing no influences of the surgical treatment procedure on the patient's eye when said second image is taken, and the eye showing influences of the surgical treatment procedure on the patient's eye when said third image is taken.

13. The method of claim 12, wherein
said influences of the treatment procedure on the patient's eye comprise one or more of the following:
bleedings,
deformations of the eyeball from the suction ring,
ablation bubbles under or in the cornea covering the iris;
color changes of the cornea or iris due to treatment impacts;
a tool or object which fully or partially occludes the eye.

14. The method of claim 10, further comprising:
performing a registration from a post-surgery images taken by said surgery device to a post-surgery diagnostic image taken by a diagnostic device; and/or
performing a registration from said diagnostic reference image to one or more post-surgery diagnostic images.

15. The method of claim 14, wherein
the registration steps are performed by identifying one or more eye features in the two eye images, which are to be registered to thereby determine the coordinate relationship between the two pictures, wherein
the eye features which are used for the different registration steps are selected in appropriately in accordance with the different modalities in the different registration steps.

16. An apparatus for performing an eye registration comprising a process configured to:
obtain a first initial reference eye image by a first diagnostic device and defining a reference coordinate system;
obtain a second eye image by a surgery device, said second eye image being obtained in a pre-surgery phase before the surgery has started; a module for performing a first registration between said first eye image and said second eye image to obtain a first registration result;
obtain a third eye image by said surgery device, said third eye image being obtained after surgery has started;
perform a second registration between said second eye image and said third eye image to obtain a second registration result;
combine said first and second registration results to obtain a combined registration result to thereby obtain a registration between said initial reference eye image obtained by said diagnostic device and said third eye image obtained by said surgery device after surgery has started
wherein said first eye image taken by said diagnostic device and said third eye image taken by said surgery device are taken under significantly different eye conditions that can negatively affect a direct registration between said first image and said third eye image, the different eye conditions comprising the eye having no tool that fully or partially occludes the eye when said first image is taken and the eye having a tool that fully or partially occludes the eye when the third image is taken.

17. An apparatus for performing eye registration comprising a processing unit configured to:
obtain a first initial reference eye image by a first diagnostic device and defining a reference coordinate system;
obtain a second eye image by a surgery device, said second eye image being obtained in a pre-surgery phase before the surgery has started; a module for performing a first registration between said first eye image and said second eye image to obtain a first registration result;

obtain a third eye image by said surgery device, said third eye image being obtained after surgery has been completed;

perform a second registration between said second eye image and said third eye image to obtain a second registration result;

combine said first and second registration results to obtain a combined registration result to thereby obtain a registration between said initial reference eye image obtained by said diagnostic device and said third eye image obtained by said surgery device after surgery has been completed;

wherein said first eye image taken by said diagnostic device and said third eye image taken by said surgery device are taken under significantly different eye conditions that can negatively affect a direct registration between said first image and said third eye image, the different eye conditions comprising the eye having no tool that fully or partially occludes the eye when said first image is taken and the eye having a tool that fully or partially occludes the eye when the third image is taken.

18. The method of claim 17, wherein said different eye conditions comprise;

the eye having no suction ring being placed on it when said second image is taken and the eye having suction ring being placed on it when the third image is taken.

19. The method of claim 17, wherein said different eye conditions comprise:

the eye showing no influences of the surgical treatment procedure on the patient's eye when said first image is taken, the eye showing no influences of the surgical treatment procedure on the patient's eye when said second image is taken, and the eye showing influences of the surgical treatment procedure on the patient's eye when said third image is taken.

20. The method of claim 19, wherein said influences the treatment procedure on the patient's eye comprise one or more of the following:

bleedings, deformations of the eyeball from the suction ring, ablation bubbles under or in the cornea covering the iris;

color changes of the cornea or iris due to treatment impacts;

a tool or object which fully or partially occludes the eye.

* * * * *